United States Patent
Even-Zohar (10) Patent No.: US 6,774,885 B1
(45) Date of Patent: Aug. 10, 2004

(54) SYSTEM FOR DYNAMIC REGISTRATION, EVALUATION, AND CORRECTION OF FUNCTIONAL HUMAN BEHAVIOR

(75) Inventor: Oshri Even-Zohar, Oostelijke Handelkade (NL)

(73) Assignee: Motek B.V., Amsterdam (NL)

( * ) Notice: Subject to any disclaimer, the term of this patent is extended or adjusted under 35 U.S.C. 154(b) by 0 days.

(21) Appl. No.: 09/401,670

(22) Filed: Sep. 22, 1999

Related U.S. Application Data (60) Provisional application No. 60/116,506, filed on Jan. 20, 1999.

(51) Int. Cl.[7] ............................. G09G 5/00; G06K 9/62; A63B 69/00; A63B 22/00
(52) U.S. Cl. ............................. 345/156; 345/8; 482/51; 382/155; 434/247
(58) Field of Search ................................ 345/156, 158, 345/8; 482/4–5, 51, 66, 78; 382/155–159; 434/274

(56) References Cited

U.S. PATENT DOCUMENTS

| | | | |
|---|---|---|---|
| 4,337,049 A | | 6/1982 | Connelly |
| 4,547,858 A | * | 10/1985 | Horak ........................ 700/261 |
| 4,649,504 A | * | 3/1987 | Krouglicof et al. ............. 345/8 |
| 5,562,572 A | * | 10/1996 | Carmein ........................ 482/4 |
| 5,623,428 A | * | 4/1997 | Kunii et al. .................... 703/6 |
| 5,768,122 A | | 6/1998 | Motoc |
| 5,785,631 A | * | 7/1998 | Heidecke ........................ 382/5 |
| 5,846,086 A | * | 12/1998 | Bizzi et al. .................. 434/247 |
| 5,930,741 A | * | 7/1999 | Kramer ........................ 702/153 |
| 6,052,114 A | * | 4/2000 | Morifuji ....................... 345/158 |
| 6,097,927 A | * | 8/2000 | LaDue ......................... 434/236 |
| 6,102,832 A | * | 8/2000 | Tani .............................. 482/4 |
| 6,119,516 A | * | 9/2000 | Hock ....................... 73/379.01 |

FOREIGN PATENT DOCUMENTS

WO     WO 97/40471     10/1997

OTHER PUBLICATIONS

Choi, Wonsu and Yoon, Joongsun, A Motion Capture and Mimic System for Motion Controls, IEEE ICAR 97, Jul. 1997, pp. 505–510.

Molet, Tom, An Animation Interface Designed for Motion Capture, IEEE Computer Animation 97, Jun. 1997, pp. 77–85.

* cited by examiner

*Primary Examiner*—Regina Liang
*Assistant Examiner*—Duc Q. Dinh
(74) *Attorney, Agent, or Firm*—Maine & Asmus (57) ABSTRACT

The present invention is a system combining motion capture technology and a motion platform with runtime interaction in a real-time feedback loop to provide a physical and virtual environment that has many applications, particularly in the rehabilitation area. The operator and user have runtime control of the system, and the data from the platform and the capture system are processed faster than real-time to generates new data sets which are then re-introduced into the system. A virtual reality environment is introduced and seamlessly interacts with the motion capture process and the motion platform operations to immerse the user in the dynamic physical and virtual environ.

18 Claims, 9 Drawing Sheets

SYSTEM FOR DYNAMIC REGISTRATION, EVALUATION, AND CORRECTION OF FUNCTIONAL HUMAN BEHAVIOR

CROSS REFERENCE TO RELATED APPLICATIONS

This application claims priority from a Benelux patent application serial number 1010150 filed on Sep. 22, 1998, from an European Patent Office application serial number 98204334.1, filed on Dec. 21, 1998, and from U.S. Provisional Patent Application 60/116,506 filed Jan. 20, 1999, which are incorporated herein by reference for all purposes.

BACKGROUND OF THE INVENTION

1. Technical Field of the Invention

This invention most generally relates to a system that combines motion capture, motion platform and simulation technology to create a fully reactive virtual and physical environment. More specifically, the present invention creates a simulated environment with real-time feedback for controlling the environment of the user. Even more specifically, the present invention incorporates operator and user runtime control with a real-time feedback loop to process data from optical and/or magnetic sensors and from a motion platform, and to generate new data sets that are introduced into the dynamic system.

2. Background of the Invention

Various studies of human motion and motor skills have contributed to methods and systems of improving motion skills and increasing the efficiency of learning motor skills. There are many applications where the increased learning curve for motion skills would be of great benefit, especially for rehabilitation purposes.

The manner in which human motion skills are learned is a complex process with continual biofeedback that begins at birth. A baby learns the physical limitations and boundaries appropriate for its size and strength, and develops the control required for manual tasks. By a constant trial and error process, a baby learns one skill set after another, in accordance with the additional size and strength development, as well as the developing mental abilities and biofeedback control. The motion skills become implanted as recognition patterns, and are recalled when that desired motion is required. The simple act of walking is actually a complex array of motions combined with biofeedback mechanisms.

The rate of learning by a baby is extremely rapid as compared to an adult adapting to new skill sets or re-learning skill sets that were lost because of an accident or medical condition. For example, a person in an accident that is outfitted with a prosthetic leg will have to re-learn the motor skills associated with walking. Balance, coordination, and the feedback control loop are altered to adapt to the prosthetic device, and it is only through a long and arduous learning process that the person will regain the ability to walk. And, the gait may or may not be natural in appearance.

There have been various attempts to utilize emerging technologies to assist in the rehabilitation process, including motion capture. Motion Capture is a term for a variety of techniques, and the technology has existed for many years in a variety of applications. The aim of motion capture is to create three-dimensional (3D) animation and natural simulations in a performance oriented manner.

In the entertainment industry, motion capture allows an operator to use computer-generated characters. The characters are used in scenes that are impractical or dangerous. Motion capture is used to create complex natural motion, using the full range of human movements and allow inanimate objects to move realistically.

Some motion capture systems provide real-time feedback of the created works and allows the operator to immediately determine whether the motion works sufficiently. Motion capture can be applied to full body motion as well as to hand animation, facial animation and real time lip sync. Motion capture is also used in medical, simulation, engineering and ergonomic applications, and in feature films, advertising, TV and 3D computer games.

Motion platforms have also been used for a variety of applications. A motion platform is a surface area that is controlled by servos, gyros, and/or actuators that manipulate the platform according to a controller. Most motion platform applications, both commercial and military, are used in simulations. The entertainment industry incorporates motion platforms in simulated rides, where a platform is manipulated to present an experience to the rider such as riding a train. Other commercial applications include flight simulations to train and test pilots with less expense and lower risk to equipment and personnel. Computer generated scenes of sequences have been used in conjunction with the platform to enhance the experience.

Virtual Environment (VE) technology primarily allows a patient to commit to a learning task. Early developments of surgical simulators have demonstrated the great potential of VE technology for training purposes. Theoretically, using VE one can record motor responses and use them to interact with and manipulate the same environment, providing an ideal tool as an approach to determine the variables involved in the execution of a motor task. VE can be used to simultaneously test, analyze, retest and train sensory and motor responsiveness.

There are many potentials and some limitations of VE computer technology to the field of clinical rehabilitation. At present there are very few documented articles on the benefits of virtual reality systems embedded into a perceptual or motor retraining program. However, it is suggested that with proper computer techniques, retraining could provide accurate measures of treatment modalities, according to the patients' progress in the rehabilitation program. The ability to produce unexpected changing goals and external forces would be of use in the field of motor rehabilitation, where virtual reality techniques can give supplemental support to the existing diagnostic loop, which requires monitoring and adjustment at all stages of therapy and recovery.

One of the major goals in the rehabilitation process constitutes of the quantitative and qualitative improvements of daily activities of a disabled person to make independent living possible. Before making up an adequate training program thorough analysis of the movement patterns is necessary. It has been proven that the best training is the so-called functional training: in order to improve a function one should train specifically this function in the way the disabled person uses it in daily living. Basic abilities, like standing and walking are already complex movements to analyze, but normal activities of daily life (ADL), like dressing, cooking or household activities, are even more complex. Still these are the goals of rehabilitation programs.

Analysis and training feedback until now are only possible for components of these activities, such as EMG feedback or balance ground floor reactions. These feedback centers are usually in a laboratory, an artificial environment that does not resemble the normal surroundings of a disabled person. There is currently no relevant artificial environment for that would simulate the actual environment of a disabled person in order to provide a more accurate and realistic training system.

Various attempts have been made to address the aforementioned problems. Prior art systems teach adaptive and motion control, which allows a user to acquire or improve motor skills by viewing and imitating recorded motions. The motion capture is typically recorded by video cameras and stored on video tape while other systems digitize the video image and the motion sequence. The user compares his motion to the recorded motion and tries to adopt the recorded motion. In these prior art applications, the user tries to emulate the recorded or reference data set. And, the prior systems do not make the user actually perform the desired motion sequence.

In U.S. Pat. No. 4,337,049, a system is disclosed wherein motion data from cameras is compared to a reference data set. An error compensation formula is used to signal the user when a threshold level is exceeded, as the user tries to emulate the visual reference.

One application described in U.S. Pat. No. 5,822,813 ('813) incorporates a motion compensated device into a bedding apparatus for a ship. The '813 invention uses a sensing means to detect the instantaneous position of the deck with respect to a reference plane. A control system commands a set of servos to keep the bed platform stable despite the pitching and rolling of a vessel.

The invention of U.S. Pat. No. 5,768,122 describes a motion platform that is controlled by an object oriented methodology. The system breaks down higher level motions into simpler tasks, and incorporates editing and a translation means to command the platform.

U.S. Pat. No. 5,846,086 describes a motor skill system wherein a teacher or model motion is recorded and played back through a virtual environment. The motion of a student is compared to the model motion, and the student tries to emulate the motion of the reference. Visual feedback in real time shows the user's motions and the reference motions, showing the user where the motions differed.

In the prior art simulation technologies, measurements are taken of a person's response time to a given simulated situation. There is no data referring to the spatial behavior of the persons in the simulation.

In addition, there has been no standard of treatment in the medical field because there has been no way to ensure repeatability in the simulation.

Motion capture studios possess a large barrier to entry because the systems are very expensive. The studios charge very high recording fees accordingly.

The recording takes a long time to produce because there is no runtime control feature. The prior art method of simulation requires an artist to render the desired experience. The engineers then implement this experience by programming, usually in assembly language, to perform according to the artist's desired experience. For example, the ride may be programmed to elevate six inches at time x, and elevate ten inches at time x+5 seconds. The engineers and artist go through several iterations lasting several months before the desired experience is recorded.

The animation produced by most motion capture also lack natural human behavioral response because it does not incorporate human motion into the processing.

None of the prior art systems incorporate a motion capture platform and simulation technology to provide a cohesive system. There is currently no means to provide real-time feedback and control of the virtual and physical environment of the user.

What is needed is a system that seamlessly integrates a physical and virtual environment, and allows a programmer to instantly manipulate and record a desired effect. The recorded effect can allow every user of the system to experience the same physical and virtual environment as the original programmer. Such a system should be affordable to operate and cost-effective to utilize.

SUMMARY OF THE INVENTION

The present invention is a motion capture system combined with a motion platform that operates in faster than real-time processing, allowing runtime interaction by the user or operator. The invention is a system that combines motion capture technologies and simulation technology, using a combination of hardware and software elements combined with the authoring and control software environment to alter the environment of the user.

The invention creates a new measurement and correction tool, bearing applications in various industries. The invention creates the possibility of immersing one or more persons in a fully reactive virtual and physical environment for determining, registering and evaluating human functional performance to a range of given situations.

Although intended for medical applications, the present invention is adaptable for other market segments.

Leisure and Entertainment—The present application provides a tool that is useful in numerous applications, including the entertainment industry. This system allows the recording of simulation rides in real-time. The system can be used to enhance and improve entertainment simulations, by providing a cost-effective and more realistic simulation. The present system allows the artist or simulation generator to create the desired effect by controlling the system and recording the desired simulation effects. The motion capture system instantly records the designers simulations and provides immediate playback. This reduces the time it takes to generate simulations from man months to minutes.

Not only is the simulation cost-effective, the system employs runtime editing and faster than real-time feedback, which can make the simulation more realistic. The operator or user can change parameters on the fly to enhance the experience. And, the movements and motions of the user can be injected into the simulation equation to make the simulation real.

Simulation rides are another application of the present inventions. Currently, engineers program simulation rides in assembly language upon direction from the artist or designer. The artist describes the desired ride or simulation, and the engineers write code attempting to replicate the artist's description. The code is written such that at time x the ride is at one position, and at time x+1 the ride is in another position. The artist then interacts with the engineers in an iterative process until the artist gets the desired result. The process typically takes several months.

In the present invention, the artist attaches the sensors to their own body and takes control of the ride, recording the simulation exactly as the artist desires. As soon as the artist is finished, the program can be played back. The artist gets the exact effect desired without the lengthy and costly engineering interface. By recording the artist's own body motions the perceived body motion can be instantly played to any user. The artist controls the platform, cutting the work and time required to generate a simulation by 99%.

Military Applications—Due to the high cost and potential danger associated with military training, simulations are becoming a preferred training method. Using the virtual reality environment with the motion platform can increase the training efficiency and improve military readiness.

Aviation and space research—The present invention allows the registration and testing of pilots and astronauts spatial coordination reaction times and latency, in real-time, while responding to an array of given simulated situations. For example, a realistic space mission can be simulated where the motions of the astronaut, the tools, and the surroundings effect the programmed environment. The zero-gravity environment can be simulated in training for space walks and missions.

Automotive—This present system records and displays in real-time the spatial trajectories of the driver movements, and creates a 3D database of these movements. The application generates data relating to a better ergonomic prototyping and design of driving environments.

Robotics and Telemetry—A telemetrically reactive environment allowing the driving of remotes in a fully interactive manner is accomplished by the present invention. The operator receives motion feedback from the remote terrain.

Architecture—The present invention allows monitoring of ground reaction to forces in earthquake sensitive buildings. The system can be employed on a large scale to support the critical sections of the building and maintain a flat platform regardless of the movement created by the earthquake.

The present invention has an enormous impact in the medical community by reducing the rehabilitation time of patients. With the great concern over health costs and regulated medical care, the present invention provides a means of lowering costs and length of treatments. It can also assist and improve the quality of life of many patients and allow the perception of physical movement for those not otherwise capable of such motion. For insurance purposes and liability, the system can aid persons susceptible to falling and improve balance and equilibrium.

The system is useful for victims of traumatic brain injury, cerebral damage, and spinal damage. The study of motion recognition supports the notion that the body remembers certain movements and can even regenerate synoptic paths. By simulating the desired movement, the body can be re-trained to make that movement. The system also enables person(s) to react to offsets in their own equilibrium, through reduction or amplification of their own motions fed back to the motion platform.

In the field of orthopedics and prosthetics, the present invention can assist patients in adjusting to their present situation. With orthopedics, prosthetics, and amputees, the system can monitor and track progress while training and improving movements. For example, if a limb is missing, the transference of momentum can correct for imbalance and train the person to be balanced.

Motion sickness and other motion disorders can be treated by replicating the conditions and allowing the patient to adjust to the motion.

The present invention not only can provide precisely repeatable measurements, but can also monitor progress of a patient by comparing recorded motions from different time intervals. It can also provide a library of standard or reference motions that can be used to highlight problem areas.

A person that has a stabilization disease, such as Parkinson's, where they are unable to stand still can be made to remain in the still position by using this system. The human body receives and processes various synoptic input for balance, it is a complex and continuous interaction, where the brain picks the best optimal input for survival as part of the biofeedback system. The user gains the perception of standing still, and medical reports state that awareness of a condition is crucial. Fear is a major component of recovery, a person that has had an accident or illness may develop a fear that prevents or hinders recovery.

The present invention demonstrates the capabilities of a person, even if the system is doing all the work. In this manner the system can help people get over certain fears. For example, if you have ever tripped on a staircase in your home, there will be a cognizant memory of that fall that may effect future trips up and down the stairs. The present invention allows the participant to cheat to overcome fear by simulating the staircase and conditions that led to the fall.

A person with a prosthetic may not wish to put pressure on the prosthetic partly because of fear and also possibly the pain. The system will deliberately put pressure on the prosthetic by raising up the platform to meet the prosthetic. Pressure sensors can monitor the pressure on the prosthetic and increase pressure to any level by changing the platform level. The virtual floor stays straight, put the physical floor in this case a treadmill, will elevate to meet the foot.

One embodiment of the present invention in relation to medical applications can serve as an example. A development project called Computer Assisted Rehabilitation Environments (CAREN), is one embodiment of the system operating in the real-time domain. The CAREN project pertains to the development of a virtual reality system in which the balance behavior of humans can be tested in a variety of reproducible conditions.

The CAREN project simulates a virtual reality environment in which the agility of healthy subjects and patients can be tested in a variety of reproducible conditions. CAREN enables measurements of motion of a subject in detail as a response to a perturbation from the computer driven motion platform. After feeding the data in a human body model simulation, joint moments of force and muscle activation can be calculated. From the time patterns of these responses, inferences can be made concerning the motor programs the subjects launch. Any primary problem in a motor program, resulting in functional failure or inadequacy, can be identified down to the joint and muscle group. Secondary problems such as lack of muscle force can be separated from the primary ones. Inadequacy of complete motor programs in children with movement disorders can be classified and recorded to track progress.

A better understanding of compensation strategies in patient's leads to a better therapy. CAREN offers not only a test environment with means of almost unlimited exploratory behaviors for patients, but also constitutes a strong tool for motor control research.

One of the major objectives of the CAREN project is to enhance diagnostic and therapeutic activities in a range of medical fields by decreasing the time needed for successful rehabilitation programs. The enhancements are defined by allowing a medical expert team the opportunity to view and analyze balance and coordination movement patterns as they happen in a controlled real-time environment. This enables the expert panel to immediately intervene and correct the patients' behavior.

The system consists of a combination of a computer controlled moving platform, a three dimensional video projection, motion capture of the subject and forward and inverse dynamics computer simulations of the movements of the subject. There is no standard rehabilitation and exercise method for diagnostic and corrective treatment of balance disorders. Most European rehabilitation clinics use specialized therapeutic programs, based on cause related classifications of movement disorders, but there is no network communicative protocol available to exchange medical experiences on used equipment and procedures. In addition, since generic tools are lacking to accurately measure the patients' behavior, progress assessment is performed mainly visually. The present invention seeks to develop an interactive virtual real-time computer drive applied tool-platform, which can provide patients with means of almost unlimited exploratory behaviors and at the same time provide medical experts accurate measurement tools for monitoring progress in the rehabilitation process.

The present invention allows for a turnkey customized visualization system for the medical sector. From the simulation industry comes a viewing environment where in the position and orientation of 3 Dimensional objects can be traced and displayed maintaining real-time speed. From the animation industry comes a 3 Dimensional toolkit for the creation and manipulation of virtual characters and environments. Developments in applying multi-threaded parallel algorithms allow for real-time integration of motion capture data and a high level of detail visualization. With the present system it is possible to measure the motion of a subject in detail as a response to a perturbation from the computer driven platform, due to the incorporation of the human body model.

The overall purpose of the CAREN project is to develop a virtual interactive system, in which the subject through a real-time biofeedback is immersed, in order to create an optimal efficient and effective rehabilitation and training situation. The enhancements are defined by allowing medical experts the opportunity to analyze balance strategies as they happen in controlled environments.

CAREN is made by customizing hardware and developing software to enable measurements of motion of a subject in detail as a response to a perturbation from the computer driven platform. The movements of the platform are performed in close synchrony with the projected images and can be independent of the movements of the subject (as when standing on a large boat) or co-depend on the movements of the subject (as when standing on a small boat).

Especially in complex balance tasks, the patterns of muscle activation determine whether a subject falls or not. These simulations are aimed at an understanding of normal or pathological response patterns in certain balance tasks.

Real-time feedback in virtually normal and responsive surroundings, created in the CAREN project, makes it possible to analyze and train disabled persons for these activities of daily life. CAREN offers not only a test- and learning environment for patients, but is also a valuable research environment for motor control. The experiments published in scientific journals are usually far removed from a natural situation. Since sensory integration is a key in understanding motor control, CAREN opens the door to a new type of experiments in which various channels of sensory input can be offered.

For example the movement control as observed in Parkinson patients is considered to be an enigma by many clinicians and human movement scientists. In these patients some visual cues are sufficient to elicit rather normal looking motor patterns (for instance used in walking), while in the absence of such stimuli a pattern can not even be started. In healthy subjects, the continuous control of balance during walking is possible by having a multi-channel sensory input onto a vast library of learned motor patterns. This input comes from mechano-receptors, such as muscle spindles, Golgi tendon organs and cutaneous receptors in the soles of the feet, as well as from the visual system. Even auditory input is helpful in establishing the nature of the direct environment in which humans walk.

The flow of the visual field is however more potent here. From experiments we know that artificial changes in the visual flow can upset the balance of subjects. An example is the moving room paradigm, in which the subject stands in a room of which the walls can be moved without moving the floor. Subjects immediately respond by an offset in their balance, sometimes resulting in a fall. In Parkinson patients, the sensory input is favored in the direction of the visual flow, while other input has become less important.

With the environments offered by CAREN, one can design experiments in which the different types of input can be adjusted. With the movable platform, sensory input through the feet can be altered, independent of the visual stimuli, and vice versa. One can let these patients walk on a thread mill of which the speed does not correspond to the speed of the visual flow field, in order to find out how various inputs are integrated and at which scaling factors. CAREN allows a better glimpse into the complexity of the natural processes associated with human motion.

Other examples can be found among patients with peripheral disorders, such as partial paralysis or paresis of a limb. In these situations, gait and balance are compromised both by a partial lack of sensory input and a lack of muscle coordination. The usual result of that is that in order to obtain a functional gait and balance the patients find compensations, resulting in deviant movement patterns in healthy parts of the body. Making use of the inverse dynamics simulations fed by the motion capture under various conditions can help to sort out the distinction between compensation and primary disorders. Humans prefer to avoid pain sensations, even if this implies a less optimal mode of walking or standing. Optimization can be sought as a compromise between functionality and comfort.

The invention is a new principle in simulation, where human behavior is evaluated or compared either to a reference behavior or to a prior behavior. This principle establishes a mechanism to achieve a simulation state whereby the persons involved are affected by their behavior, and by the physical and the visual environments in which they are immersed.

The composition of real-time full body capture and a controlled "ground" creates the capacity to use motion capture for the creation of complex animations which include interactions between the character and the environment.

The motion capture solution also allows performance animation devices. A turnkey capture solutions have added to the capture and control utilities a 6DOF motion platform output channel driver, it allows the control and the programming of motion rides and simulation scenario's directly from the system.

A further feature of the present invention is facial capture. Using a combination of key mouth shapes and a comparing batch of libraries, it is possible to create realistic or cartoon mix of capture and animation. The FACE-MIXER is a channel driver for SOFTIMAGE allowing mixing while recording, facial expression animation in a LIVE capture situation. It uses radial shape influence, which means that all the keyshapes are active at all times. The animator controls the range of expressions, the speed of change and the trajectory from one expression to another.

An object of the invention is a motion processing system, comprising a processing means, a motion capture system connected to the processing means. The motion capture data is taken from a plurality of motion sensors and s processed faster than real-time. There is a motion platform system connected to the processing means, wherein motion platform data is also processed faster than real-time, and wherein control commands are output to the motion platform. There is also a means of interfacing to the motion processing system with a runtime control input.

A further object is a motion processing system, wherein the plurality of motion sensors is optical. Additionally, the motion processing system can have a plurality of magnetic motion sensors. A combination of optical and magnetic sensors is also within the scope of the invention.

And a further object is a motion processing system further comprising a display means for displaying a virtual environment to a user, wherein the displaying means is connected to the processing means. The display means could be stereoprojection or headmount display, and create a virtual environment in tandem with the physical manipulated environment.

An additional object is a motion processing system, further comprising a memory means for recording the motion capture data and the motion platform data. The recorded data can be played back and simulate exactly the environment that was recorded in real-time. The virtual environment can also be recorded in conjunction with the motion data to complete a total immersion environment.

An object of the invention is a virtual and physical environment process, comprising the steps of placing a plurality of markers on a user, positioning the user on a motion platform, receiving a motion capture data set from the plurality of markers, receiving a motion platform data set from the motion platform, inputting control signals in runtime, processing the control signals, the motion capture data set and the motion platform data set in a faster than real-time format on a host computer system, and outputting a new data set to the motion capture system and the motion platform system. A further object includes a virtual and physical environment process further comprising the step of displaying a virtual reality environment for the user.

Another object is a virtual and physical environment process wherein the step of inputting control signals in runtime is performed by the user. The operator or user, or both can input changes to the dynamic system.

An object of the invention is a simulation recording system, comprising a user outfitted with a plurality of motion sensors and stationed on a motion platform. There is a processing means, and a motion capture system connected to the processing means, wherein motion capture data from the motion sensors is processed faster than real-time. A motion platform system is connected to the processing means, wherein motion platform data is processed faster than real-time, and wherein control commands are output to the motion platform. The system also has a means of interfacing to the processing means with runtime control input, and a memory means for recording the motion platform data and the motion capture data. This system allows the operator/artist to design the desired simulation in real-time without resorting to engineers and programming. And yet another object is a simulation recording system, further comprising a means of playing back the recorded motion platform data and the motion capture data from the memory means.

There is an added object wherein the simulation recording system, further comprises a means of recording a virtual reality environment in sequence with the recorded motion platform data and the motion capture data.

A system for dynamic registration, evaluation, and correction of functional human behavior, comprising, a memory means, a motion platform system, wherein a user is stationed on the platform. There is a motion capture system, wherein the user is outfitted with a plurality of markers to detect motion, and a processing means connected to the motion platform system and said motion capture system, wherein motion platform data and motion capture data is processed faster than real-time by said processing means, and wherein new control data is output to the motion platform system. Finally, there is a means of recording the motion capture data and the motion platform data on the memory means, and a means of interfacing to the system with runtime control input.

Another object includes playing back of the recorded motion capture and motion platform data from the memory means to generate external forces on the user. The motion platform generates inverse forces to make the user regenerate the recorded motion.

And a final object is a system for dynamic registration, evaluation, and correction of functional human behavior, wherein the memory means contains a library of previously recorded data. The data can be from a library of reference motions and environments or a library of data recorded for an individual user so that progress can be monitored.

Still other objects and advantages of the present invention will become readily apparent to those skilled in this art from the following detailed description, wherein only a preferred embodiment of the invention is described, simply by way of illustration of the best mode contemplated for carrying out the invention.

DESCRIPTION OF THE PREFERRED EMBODIMENT

To those skilled in the art, the invention admits of many variations. The following is a description of a preferred embodiment, offered as illustrative of the invention but not restrictive of the scope of the invention. As will be realized, the invention is capable of other and different embodiments, and its several details are capable of modifications in various obvious respects, all without departing from the invention.

Figure 1:
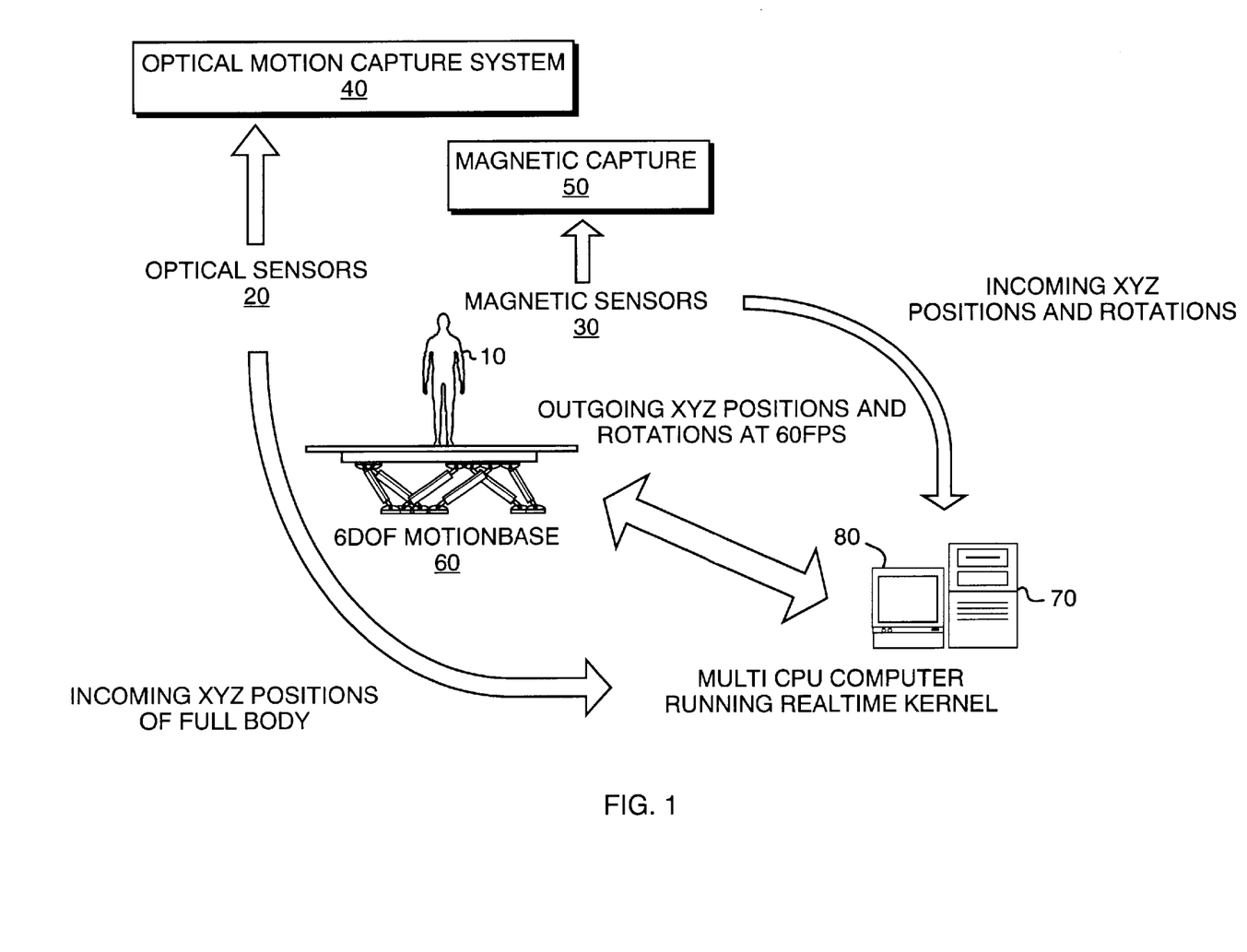
FIG. 1 shows the basic interrelationship between the motion platform, motion capture systems and computer.

FIG. 1 illustrates an overview of the present invention wherein a user 10 is equipped with a number of optical sensors 20 and magnetic sensors 30 attached at various locations of the body. The data from the optical sensors 20 is received by the optical motion capture system 40. The data from the magnetic sensors 30 is received by the magnetic motion capture system 50.

In a preferred embodiment, the optical data set contains the X axis, Y axis, and Z axis positions of the user 10 for the full body, and is transmitted at 100 FPS to the computer 70. The magnetic capture data set containing X axis, Y axis, and Z axis positions and rotations of the user 10 is transmitted at 60 FPS to the computer 70.

The computer 70 interactively operates with operator interface 80 and transmits X axis, Y axis, and Z axis positions and rotations at 60 FPS to the 6DOF platform 60.

The magnetic system involves the use of a centrally located transmitter, and a set of receivers 30, which are strapped onto various parts of the person 10. These receivers 30 are capable of measuring their spatial relationship to the transmitter. Each receiver 30 is connected via cable to an interface that can be synchronized so as to prevent a data skew. The resulting data stream consists of 3D positions and orientations for each receiver 30.

This data is typically applied to an inverse kinematics platform to drive an animated skeleton. Magnetic systems are effected by any sizable areas of metal in vicinity of the capture-area, so proper shielding is important.

The magnetic capture platform operates with the magnetic sensors 30 to register positions and orientation of the object in space. Although optical capture 40 and magnetic capture 50 can be used concurrently, magnetic capture 50 is most appropriate in situations where optical capture 40 is difficult or in multi actor shots.

Figure 2:
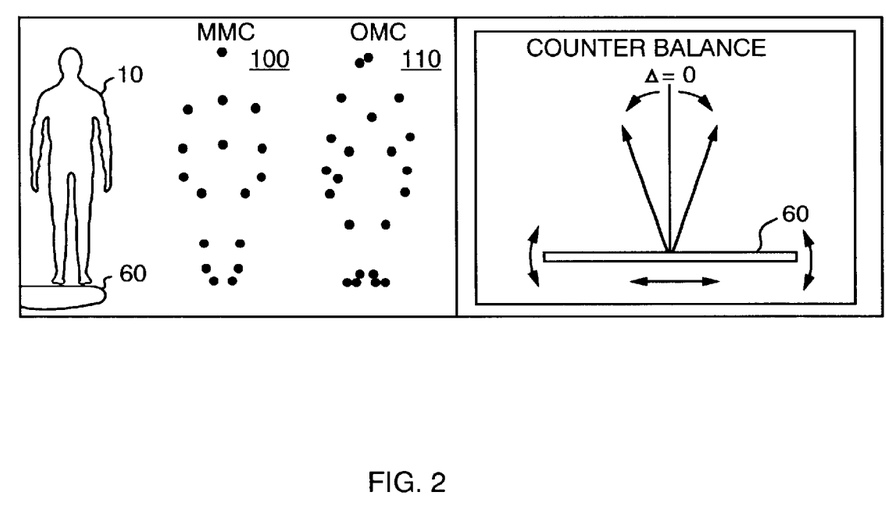
FIG. 2 illustrates a counter balance application.

Referring to FIG. 2, a person 10 is outfitted with markers 20, 30 and a template is processed for an initial or balance position. Both optical markers 20 and magnetic markers 30 are typically used to record the motion. The magnetic motion capture (MMC) data set 100 and the optical motion capture (OMC) data set 110 are instantaneously captured, and used to process a complete template. The template utilizes a template matching algorithm to interpolate for missing or bad marker data. The motion platform 60 can be programmed in any DOF to compensate for accumulations of offsets from the initial or balance point, where the delta=0.

For example, if a person 10 leans forward, the system would respond faster than real-time and adjust the platform 60 so that the OMC data set 110 and MMC data set 100 would remain in the same position.

The human visual perception rate ranges between 18–30 Hz. The balance or equilibrium rate is much slower, and is approximately 7–8 Hz. In the industry, real-time is defined as being in the 25 Hz or 25 fps range. The present invention operates at speeds much greater than real-time, and in a preferred embodiment operates at 100 Hz. Higher speeds are possible and would be a realistic expectation as the technology and computing hardware progresses.

The platform 60 is capable of six (6) degrees of freedom (DOF) in the preferred embodiment. Each DOF is independently controllable through the various servos and controllers of the platform 60.

Figure 3:
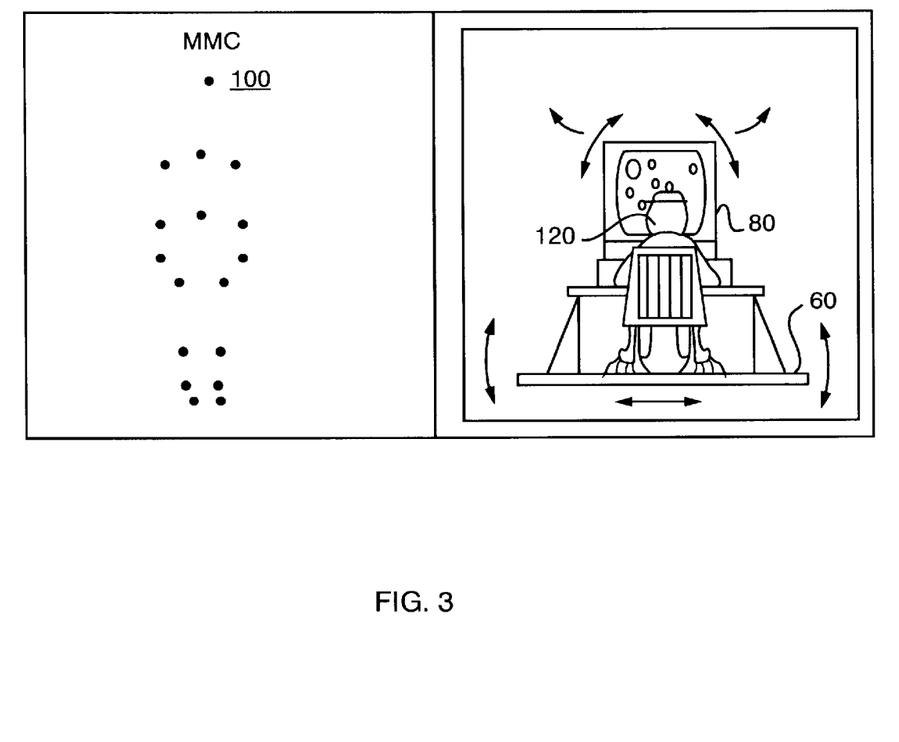
FIG. 3 illustrates an instantaneous simulation recording application.

FIG. 3 shows a different application of the present invention, wherein the MMC data set 100 recorded by the operator 120 allows real-time recording of virtual camera trajectories (eg: simulation rides) containing the body motions of the operator 120. These recorded perceived body motions can then be programmed so that all future users can experience the same body motions as those recorded by the operator 120. The operator 120 employs the computer interface 80 to input runtime commands to the system. This allows the artist/operator the ability of instantly recording the desired experience for the simulation without involving lengthy and costly engineering intervention.

Figure 4:
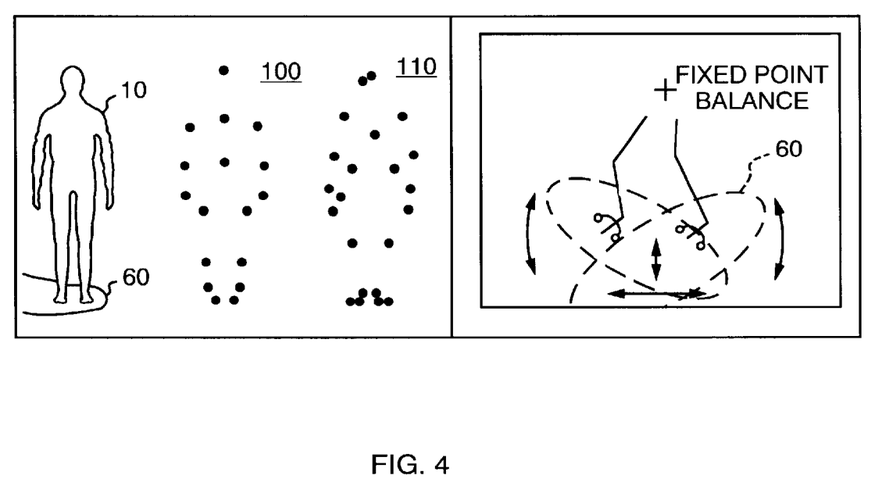
FIG. 4 illustrates an inverse force application.

In FIG. 4, the template is used to create inverse platform forces to generate external forces to act on the person 10 on the platform 60. The person will perceive the desired motion without actually performing the tasks.

There is much experimentation being done with memory recognition as a training tool for those paralyzed. An example is for a person with spinal or cerebral damage leaving the legs paralyzed. The person is hung from a sling over the platform 60 and the system applies inverse forces to make the legs move. The perceived walking motion may implant memory recognition in the person that would facilitate recovery.

Figure 5:
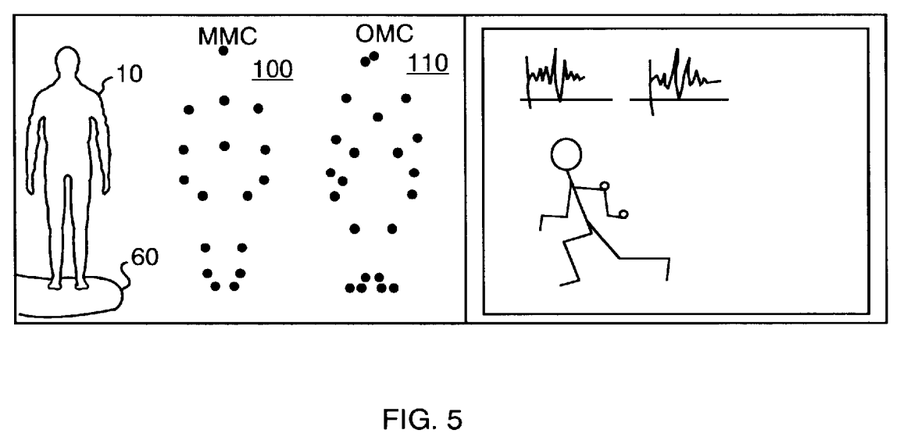
FIG. 5 illustrates a virtual clone application.

The virtual clone is embodied in FIG. 5, where the data set 100, 110 and template of a person 10 can be compared to the data set 100, 110 and template of a healthy person or another data set 100, 110 and template of the same person at a different time period. This comparison is useful for tracking progress and to identify potential problems. A real-time generation of comparative motion values can be graphed as a real-time datastream of X, Y, Z values.

It is also possible to project a virtual character data set for showing library data compared to subject motion. A motion capture reference library can be established containing the data set of individuals performing various tasks. It is then possible to take the data of subject motions and overlay the user data as compared to a library reference. It is also possible to make the user match the stored data set.

As an example, the motion capture data set of Mark McGuire swinging a bat can be recorded by the system. Any user can then compare their data set to this reference. Furthermore, the system can be invoked to make the person match the reference data set. In other words, the person would be forced to swing the bat like Mark McGuire.

Figure 6:
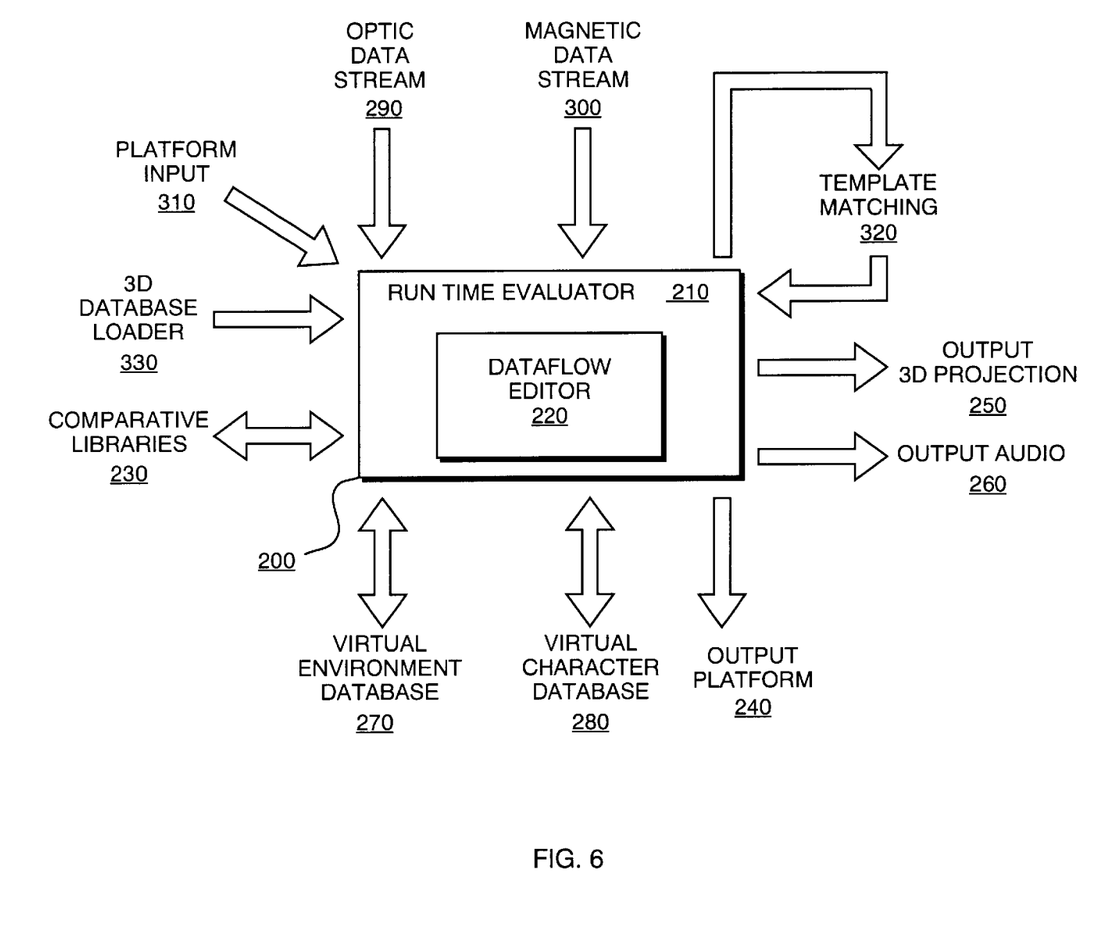
FIG. 6 is a block diagram of the D-FLOW architecture.

FIG. 6 is a basic diagrammatic view of the software architecture illustrating the various interconnections. The dataflow module (D-FLOW) 200 is a vital component of the system and supports various alternatives and allows rapid development and implementation of new features of the system. D-FLOW 200 is characterized by it's modules, implementing well defined functionality, receiving and/or sending data through zero or more input/output ports as well as the connections between the various modules, forming a directed a-cyclic graph. The main tasks of D-FLOW 200 are processing the input data coming from the various input devices, mapping the collected data into the human body model, and processing the various input and/or computed data depending on different cases. Other tasks include the display of real-time graphic animations of human models and environments, as well as driving the motion platform itself.

The D-FLOW module 200 functionality is defined by the building blocks represented by the runtime evaluator 210 and the dataflow editor 220. The dataflow editor 220 permits editing, connecting and disconnecting of the D-FLOW 200 modules while executing in runtime. This editing can be done by a system programmer or by the user while in the record mode. For example, if the simulation is for a boat of medium size on average sea conditions, the dataflow editor 220 permits the programmer or user to change the size of the boat or the sea conditions.

The runtime evaluator 210 is part of the fast feedback loop that continuously monitors the user's motion on the platform and interacts the user's motions into the system to create a realistic dynamic environment. In the boat example, if the user leaned to one side of the boat, the system would react to that movement in faster than real time and pitch the boat in that direction via the platform output commands 240 similar to what would happen in a real boat. And, by using the dataflow editor 220 in runtime, the user can change the size of the boat, thus raising the instability of the boat. In a smaller boat, the same leaning motion would have a greater impact on the boat and it would pitch further.

As part of the motion capture system, a comparative library 230 of different recordings is developed and used to reproduce certain motions or movements, compare various models, or to track progress of a patient.

The various outputs of D-FLOW 220 include the stereo 3D projections 250 and any corresponding audio output 260. The faster than real time feedback allows the user movement to interact with the virtual environment and enhance the simulation experience. A virtual reality environment may include a headmount display unit.

The various input/output (I/O) are shown, and the arrows indicate the data flow. The optic data stream 290 from the optical motion capture system and the magnetic data stream 300 from the magnetic capture system are inputs to the D-FLOW 200. Platform data 310 is also input to the D-FLOW 200 to keep track of the platform orientation.

The virtual character database 280 and the virtual environment database 270 contain recorded data sets from previous motion capture tasks. These libraries can be used in future applications to speed up the development of a project. The 3D database loader 330 is also interconnected to the D-FLOW module 200.

The template matching algorithm 320 predicts the positions of markers that are missed from a specific sample, by using forward dynamics. The simulations reconstruct the moments of force produced around the joints of the subject, which in their turn depend on muscle activation. If a marker is missed, the torque is computed from the higher level in the model hierarchy and applied to the missing marker position.

Since robust capture data is crucial for the performance of the system, special attention is put on a dynamic capture template matching algorithm 320. This algorithm 320 predicts the positions of markers that are missed from a specific sample, by using forward dynamics simulations performed with a 15 segment three-dimensional human body model. The simulations reconstruct the moments of force produced around the joints of the subject, which in their turn depend on muscle activation. If a marker is missed, the torque is computed from the higher level in the model hierarchy and applied to the missing marker position.

Figure 7:
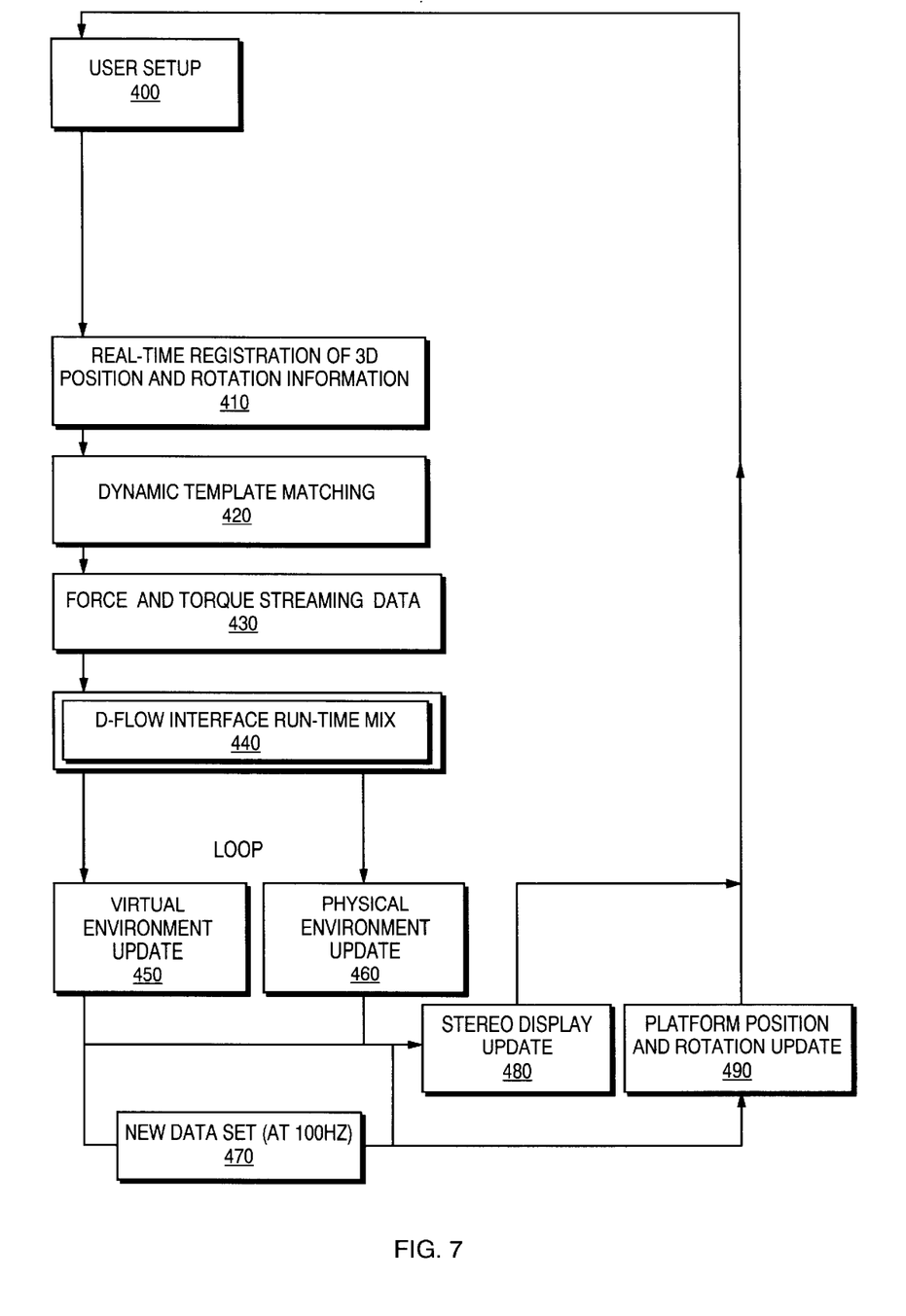
FIG. 7 is a flow chart of an application showing the interrelated elements.

The flowchart of FIG. 7 along with FIG. 1 illustrates the process of one embodiment of D-FLOW. During user setup 400, the user 10 mounts the platform 60 and is outfitted with custom markers, either optical markers 20, magnetic markers 30, or a combination of the two. The markers 20, 30 are customized for the particular application.

The optical motion capture system 40 and magnetic motion capture devices 50 are engaged 410 to capture the data sets. The real-time registration of the 3D position (X, Y, Z-axis) and rotational information is sent to the computer 70 for processing.

The data set is dynamically matched to the template 420 and the force and torque streaming data 430 is continuously measured. The streaming data 430 is analyzed by the D-FLOW interface and run-time mix 440, which interactively controls the virtual environment updates 450 and the physical environment updates 460 from the measured data as well as any operator or user commands.

The new data set 470 created by the D-FLOW interface is used to update the stereo display 480 or other virtual viewing means such as headmount display. The platform position and rotation information is updated and sent to the motion platform 420. The feedback loop is continuous at a faster than real time speed of 100 Hz, and responds and reacts not only to the user's movement, but also to user/operator runtime commands.

Figure 8:
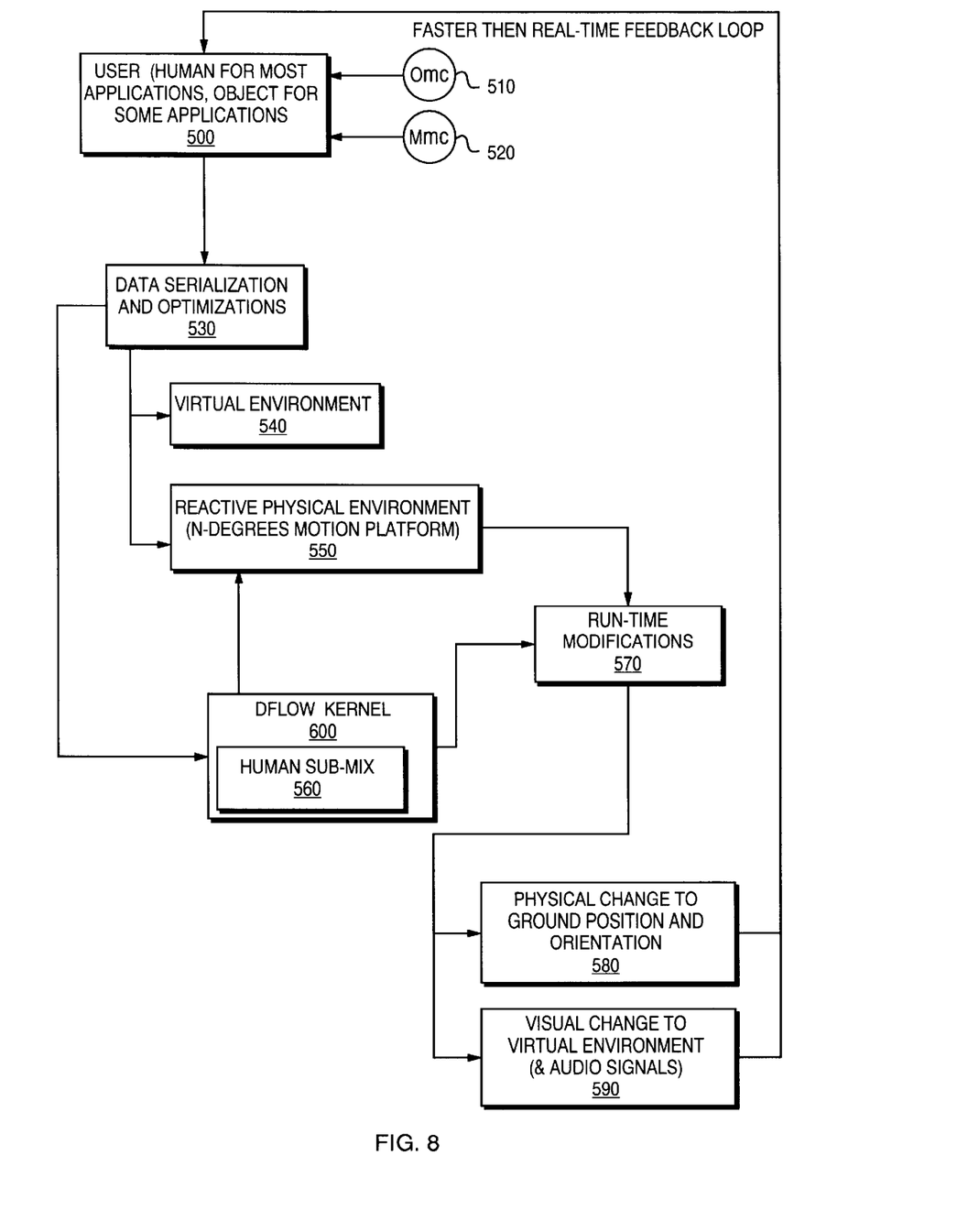
FIG. 8 is a flow chart of an application showing the interrelated elements.

FIG. 8 shows the interconnection of the overall system. The user 500 employs markers and motion capture systems to generate a corresponding data set of optical motion control data 460 and magnetic motion control data 465. The user 500 is typically a human involved in medical applications or simulation, but the system can also be used for objects such as an earthquakeproof building. The data sets 510, 520 consist of coordinates relating to the X axis, Y axis and Z axis position and rotational data, and is transmitted in faster than real time speed to the data serialization and optimization section 530.

The desired system conditions are issued to enable the virtual environment 540 and the reactive physical environment 550. The virtual environment 540 could be a headmount display or stereo projection, while the physical environment 550 could be the N-degree motion platform. All this information is fed through the D-FLOW kernel 600, which processes the data using a human submix 560 to produce the dynamic real-time system with realistic motions. The D-FLOW kernal 600 interacts with the user data and any run-time modifications 570 to produce the physical change to the ground position or orientation 580 as well as the visual change to the virtual environment 590. The physical and virtual changes are fed back to the user via a faster than real-time loop.

Figure 9:
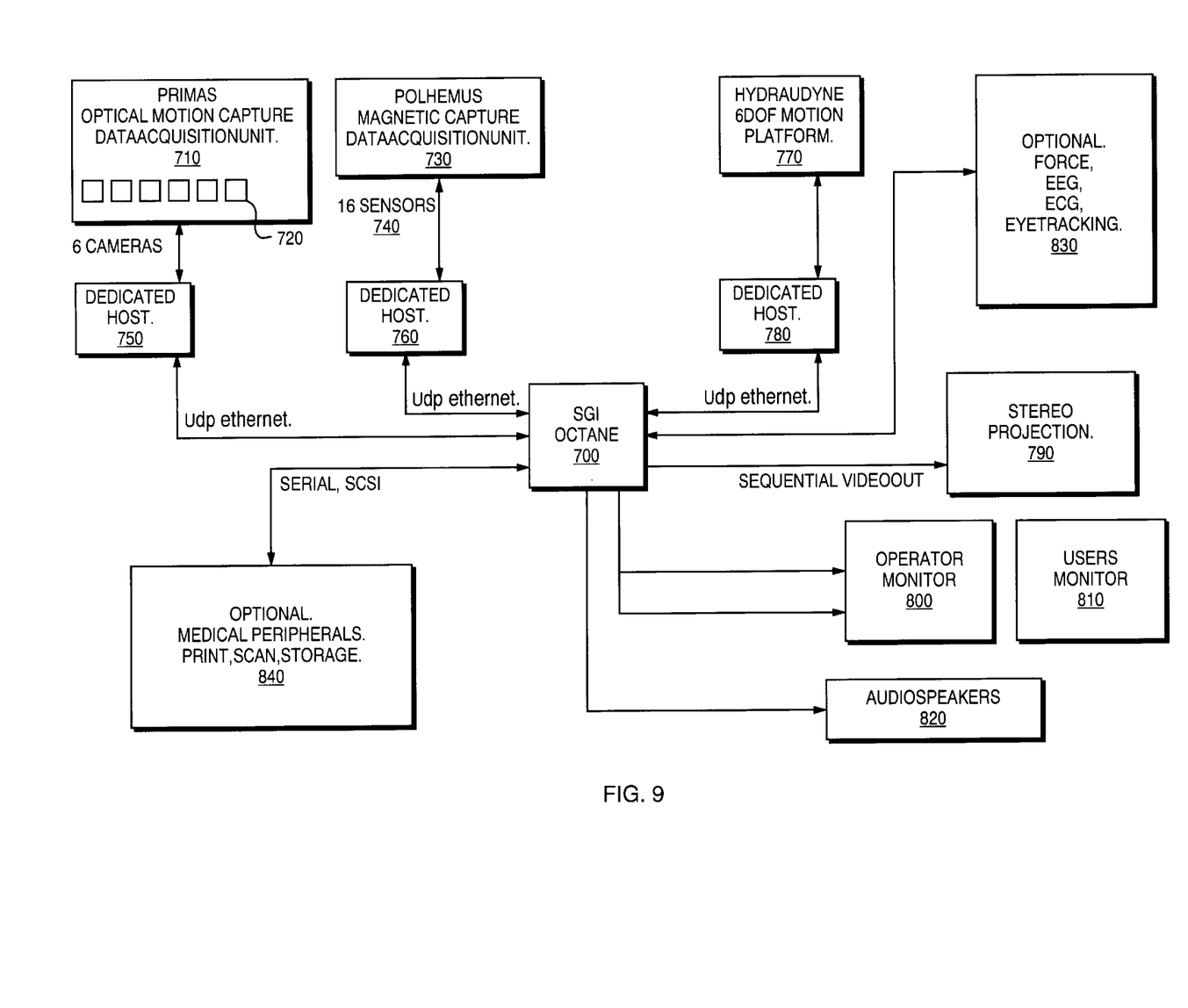
FIG. 9 is a depiction of the hardware components of one embodiment.

FIG. 9 is a block diagrammatic view illustrating the hardware connections of one embodiment of the present invention. The hardware platform is based on Silicon Graphics workstations and Intergraph Multi-processor workstations. Data capture is handled by an 8CPU Onyx and an OCTANE dual CPU.

The multi-CPU hardware platform (SGI Dual CPU OCTANE MXE) 700 is used as the computer means for processing, memory, and interface. The various peripherals and communications are accomplished by using standard high-speed connections using Ethernet, serial, and SCSI connections to dedicated hosts. The dedicated host can be a separate personal computer (PC) or an integrated on-board computer that interfaces with the peripheral equipment.

The optical motion capture system 710 includes six cameras 720, and the data acquisition unit of the optical motion capture system translates the camera input into the desired data set. The data set is the OMC data obtained from the optical marker set, and is accessible to a dedicated host 750 that allows for the fast exchange of data to the CPU 700. Data is delivered at any required file format.

The main optical capture system is PRIMAS, and is readily configurable for many setups. PRIMAS is capable of converting and displaying 3D data coordinates of up to 80 optical markers at 100 HZ, which is very useful for multi characters interaction shots. PRIMAS operates well at extreme conditions (direct studio or location lighting, smoke, and sunlight.) PRIMAS cameras have a set of lenses allowing for a wide range of capture volumes, and multiple systems can be used in parallel to accommodate complex structures. The system can be triggered externally making it easy to sync to film cameras or other devices. Calibration times are short, post processing is done using custom SOFTIMAGE next to KAYDARA's FiLMBOX optical module.

The magnetic capture unit 730 houses the magnetic capture data acquisition unit that translates the data gathered from the various magnetic sensors 740. The data set is accessible to a dedicated host 760 that is interconnected to the CPU 700. The magnetic capture platform of the present embodiment is the ULTRA-TRAK from POLHEMUS.

The motion platform 770 is interconnected to dedicated host 780 that connects to the CPU 700 for transferring data and control information. The platform of the preferred embodiment has six degrees of freedom (6DOF), and any and all of the degrees are controllable by the system.

Stereo projection 790 can be used independently or in conjunction with the platform to create a virtual environment for the user. A sequential video connection between the CPU 700 and the stereo projection 790 allows the system to run the virtual scenario. The user can choose between the various virtual environment tools, such as headmount displays and widescreen stereo projection. The headmount displays do provide a greater peripheral virtual environment, which is more immersive for the user.

There are interface and control means provided by an operator monitor 800 and a user monitor 810 in the preferred environment. The CPU 700 is directly connected to the monitors and allows runtime changes to the executable code to change conditions within the platform or virtual environment.

Audiospeakers 820 are connected to the CPU 700 and allow for a variety of audio interfaces with the user. The audio can be used to provide an indication of performance or stimulation. A sinewave generator can be used to provide a pitch for calibration, the system can generate a noise to indicate boundaries of a virtual wall, and environmental stimuli can be introduced.

There are numerous optional peripherals 840 that can be implemented and connected to the CPU 700 that would allow manipulation and presentation of the data. There are also optional applications 830 that can be interconnected to perform such functions such as eyetracking and electrocardiogram (ECG).

In operation, a person is situated on an N-degree motion base. The motion base can be electric, hydraulic, or a combination system. The only requirement for the motion base is that is respond to commands at a high rate. The person has markers, optical, magnetic, or a combination of the two that are used to track and monitor movement. Positional and rotational data of the person's full body is transmitted to a fast computer at a rate above 25 frames per second (FPS). The data generated by the person's motion is sent to a fast processing unit, then mixed and partially sent back to the motion base. These processes are running at speeds above 25 FPS. The system responds to the persons accumulating offsets of equilibrium, either through correction or through amplification (positive or negative vector modifications). The response of the N-degrees of freedom (N-DOF) motion base is application dependent and is fully user configurable through the use of the runtime kernel user interface.

At the core of the present invention is the feedback loop created when data generated from the person's motion influences the simulation. A full data set of the spatial behavior of the persons motions are registered and compared in real-time with the perceived optimal behavior. The simulation conditions are dependent on the person's activities. The instructor gets information not only about the response time to a given simulation scenario, but also the reasons why the response took that length of time. This bears direct application on ergonomic spatial design.

The fast feedback algorithm, called D-FLOW, processes the incoming data at a speed greater than the real-time standard of 25 Hz. The incoming data is in the form of motion capture data from a person, whether full body or partial. Motion data is obtained by using markers, primarily 2 types—Optical and Magnetic. In a typical application there are 25 optical markers and 11 magnetic markers, although it varies depending on desired purpose, and can use 60 markers for redundancy. In some instances, partial body data may be the only area of interest.

For example, with Parkinson's disease, the purpose may be to specifically evaluate the hand of the patient. In that case, markers would be placed at various locations about the hand and the motion capture data would be recorded. Parkinson's disease has been analogized to a feedback loop in electronics. Normally the brain and body coordination work in conjunction so that as a person reaches for a glass the brain processes the various inputs and ensures that the hand grasps the glass. With Parkinson's, the feedback of the inputs is not properly processed and the hand shakes because the brain and hand are not synchronized. The hand is constantly over and under compensating, resulting in shaking.

In operation, a person is rigged up with markers. Motion capture data is recorded by the system. There are several manufacturers of motion capture platforms, and the present invention is not specifically tailored to any individual make or model. The system captures and processes the data regardless of motion capture system used. Data is data, and the data comes into computer system and while it is coming in—stream time—the data is manipulated. Portions of the data, depending on the operator choice, objective, and control is patched directly into the control loop section that controls the motion platform. The various ways of controlling the platform are a function of the captured data. If someone moves forward, the platform can move up in faster than real time to compensate for that movement. The interface is generic, and the software modules are connected to one another and the various inputs corresponding to various outputs.

Part of the data is piped through a human submix. This submix is unlimited, and receives data in from human body in approximately 40 degrees of freedom. The system can assign/link these 40 degrees of freedom into whatever output of any set of the 6DOF of the platform, stereoprojection, or immersive virtual environment.

The D-FLOW allows data coming in and going out in stream time while mixing, manipulating, or assigning functions, or expressions or modulation, such as changes in frequency or time to that data. The output or end result of the processing can be to a platform, stereo projection, immersive virtual environment, or similar technological device. The output technology is flexible, the data can be used by any new technology. From a programmer's viewpoint, D-FLOW allows the user to modify the executable on runtime. Normally this cannot be done, for example the executable word processing program of Microsoft Word does not allow runtime changes to the executable portions of the software. Because D-FLOW connects module to module to module . . . it can connect or disconnect any module, it can edit or change the functionality of any module while it is running.

D-FLOW deals with the various inputs and outputs in a speed that is faster than real time and allows the human submix—changing the parameters while the program is running. The D-FLOW code is based upon LaGrange equations, and the system is dynamic and needs to be operating several times above real-time to evaluate something that runs at real-time.

The human submix can be further explained by example. In a boat environment, the user can interact with environment and modify the platform representing the boat. In one situation, the boat is programmed with waves in 5 out of 6 degrees, where the 6th degree is roll. The operator can scale waves up or down, or the boat up or down. If the person moves, the boat will interact and respond to the person's motion just like in a real boat. The amount of roll will depend on the size of the boat and the force exerted by the person as well as any other parameters that might be applicable. This differs from ordinary motion simulators that merely respond to set programs and allow some control of the program but not with real time feedback. Amount of channels of freedom given to the person can vary and the person can control any or all of the degrees of freedom.

As a further example involving counterbalance, where a person is made to stand perfectly still on the platform. In reality, an average person standing still actually moves 1–2 mm and continually moves as the body uses its internal feedback loop to maintain a relatively still position. A person with Parkinson's disease may have 4–5 mm sway. The D-FLOW software can amplify the user's motions by 4–5 times and record the curves. This makes the analysis and comparison of the motions easier to perform. This motion can be analogized by trying to balance a stick on your finger. You continually act/react to the changes and compensate to keep the stick upright. As part of a feedback mechanism there is a continuous pattern that can be recorded. The curvature of the motion of the balancing stick is exactly the same as the curvature of a person trying to remain still.

Placing 2–3 sensors on the shoulders of a person, the platform can be used to respond faster than the body's feedback mechanism, and will continue to move to keep the sensors in the 0,0,0 position. If the motion capture system picks up data that the person leans a little forward, the platform responds faster than the person and raises the forward degree of freedom to keep the person in the same 0,0,0 position.

The forward dynamics simulations can be done at any time during an inverse dynamics simulation. The flow of movements as an input to the inverse dynamics simulation is stopped during a sequence and the calculated joint movements are now used as input, while the movements become output. Thus forward simulations calculate movements and reaction forces from moments of force produced around the joints of the subjects.

The core of the dynamic simulations consists of a large set of LaGrange equations. These are called the equations of motion, which contain the relation between the generalized forces applied at the body and the generalized movements. "Generalized" in this respect means that they are formulated along the movement possibilities (or degrees of freedom) of the human body, rather than in terms of forces in the external world. This implies that most of the generalized forces are actually moments of force (or torque). Equations can be added describing the kind of interaction with the environment, such as contacts with the floor. The equations can be solved simultaneously in a forward simulation, solved algebraically in an inverse simulation or rearranged and solved to do a mixed inverse and forward simulation.

From this the location of the center of mass is calculated, which, together with the position of the feet, can be used to drive the motion of the platform, if this is required by the virtual environment. The human body model produces the joint moments of force of the subject, which can be evaluated against a stored library of common patterns of joint moments. If necessary, this information can be offered in the projected image to be used by the subject. When problems arise in the functionality of the movement or balance, a forward dynamics simulation can be started to indicate where weak parts in the motor pattern are located. These models allow for easy expendability and high performance of the system.

The CAREN system combines the following elements: Hardware: Optical Motion capture system with electromagnetic tracking device; multi-CPU hardware platform (SGI Dual CPU OCTANE MXE), 6DOF motion platform and Dual head option and video I/O. To support various scenarios and to allow rapid development and implementation of new features of the system, a dataflow model is chosen for the core of the system. A dataflow system is characterized by it's modules, implementing well defined functionality, receiving and/or sending data through zero or more input/output ports as well as the connections between the various modules, forming a directed a-cyclic graph.

The main tasks of D-FLOW are processing the input data coming from the various input devices, mapping the collected data into the above mentioned human body model, processing the various input and/or computed data depending on different cases. Other tasks concern the display of real-time graphic animations of human models and environments, as well as driving the motion platform itself.

The software is written in C and C++ with SGI Performer 2.2, a software platform that has proven performance in real-time applications, and has low level control over parallel system operations. D-FLOW has several modules, and the various module structures and interconnecting modules allow the executing software processes to perform runtime connections, edits, and disconnects to the system.

The SoftLoad module imports scenes from Softimage3D, containing geometry of characters and environments, I/O channel connections, IK skeletons of characters, lighting setup and textures. The Camo module coordinates the dataflow through online human sub-mix, into the various outputs. Perfly, the SGI based performer display viewing environment, allows for extensive debugging and optimizations in run-time. The system is not constrained to a single computer, by using CORBA, a standard architecture for connecting heterogeneous computing environments, modules can be implemented in any computer language or system supporting CORBA.

The user interface for the operator, is implemented in Java, using Java-Beans as the means to communicate with D-FLOW through the CORBA interface. As an example of operation, after having decided on the type of virtual environment to simulate, the visual part of the environment is projected in 3D on the screen in front of the subject, wearing 3D shutter glasses. The user stands on a platform or tread mill, which can be controlled as part of the virtual environment or as a reaction to movements of the subject. The user wears optical and/or magnetic markers of which the position and orientation are recorded. These are fed into an algorithm that turns them into the degrees of freedom of the human body model, which is filled with the segment masses and inertia of the subject.

From this the location of the center of mass is calculated, which, together with the position of the feet, can be used to drive the motion of the platform—if this is required by the virtual environment. The human body model produces the joint moments of force of the subject, which can be evaluated against a stored library of common patterns of joint moments. If necessary, this information can be offered in the projected image to be used by the subject. When problems arise in the functionality of the movement or balance, a forward dynamics simulation can be started to indicate where weak parts in the motor pattern are located. These models allow for easy expandability and high performance of the system.

The foregoing description of the preferred embodiment of the invention has been presented for the purpose of illustration and description. It is not intended to be exhaustive or to limit the invention to the precise form disclosed. Many modifications and variations are possible in light of the above teachings. It is intended that the scope of the invention be limited not by this detailed description, but rather by the claims appended hereto.

What is claimed is:

1. A motion processing system with interactive real-time biofeedback, comprising;
   a motion capture system producing motion capture data from a plurality of motion sensors;
   a motion platform system and producing motion platform data;
   a processing means coupled to said motion capture system and said motion platform system, processing said motion capture data and said motion platform data using forward dynamic simulations to predict moments of force and generate control commands in response thereof to provide a reactive physical environment and said real-time biofeedback.

2. The motion processing system according to claim 1, wherein said plurality of motion sensors is optical.

3. The motion processing system according to claim 1, wherein said plurality of motion sensors is magnetic.

4. The motion processing system according to claim 1, wherein said plurality of motion sensors is optical and magnetic.

5. The motion processing system according to claim 1, further comprising a display means for displaying a reactive virtual environment to a user, wherein said display means is connected to said processing means.

6. The motion processing system according to claim 1, further comprising a memory means for recording said motion capture data and said motion platform data.

7. A virtual and physical environment process to provide real-time biofeedback, comprising the steps;
   placing a plurality of markers on a user, wherein said markers arc coupled to a motion capture system;
   positioning said user on a motion platform;
   generating a motion capture data set from said motion capture system;
   generating a motion platform data set from said motion platform;
   inputting control signals in runtime to said motion platform and said motion capture system;
   processing said control signals, said motion capture data set and said motion platform data set on a host computer system using forward dynamic simulations to predict moments of force of said user; and
   outputting a new data set to said motion capture system and said motion platform in response to said forward dynamic simulations to provide said real-time biofeedback with a reactive physical environment.

8. The virtual and physical environment process according to claim 7, further comprising the step of said motion capture system displaying a reactive virtual reality environment for said user.

9. The virtual and physical environment process according to claim 7, wherein said step of inputting control signals in runtime is performed by said user.

10. The virtual and physical environment process according to claim 7, wherein said step of inputting control signals in runtime is performed by an operator.

11. A simulation recording system, comprising:
    a user outfitted with a plurality of motion sensors and stationed on a motion platform;
    a processing means;
    a motion capture system connected to said processing means, wherein motion capture data from said motion sensors is generated;
    a motion platform system connected to said processing means, wherein motion platform data is generated;
    an interface means coupled to said processing means with a runtime control input;
    a memory means for recording said motion platform data and said motion capture data; and
    a means for playing back said recorded motion platform data and said recorded motion capture data from said memory means and processing said motion capture data and said motion platform data using forward dynamic simulations to predict moments of force and generate control commands in response thereof to provide said real-time biofeedback with a reactive physical environment.

12. The simulation recording system according to claim 11, wherein said user operates said runtime control input.

13. The simulation recording system according to claim 11, further comprising a means for recording a reactive virtual reality environment in sequence with said recorded motion platform data and said recorded motion capture data.

14. A system for dynamic registration, evaluation, and correction of functional human behavior, comprising:
    a motion platform system, wherein a user is positioned on said platform;
    a motion capture system, wherein said user is outfitted with a plurality or markers to detect motion of said user;
    a processing means connected to said motion platform system and said motion capture system, wherein motion platform data and motion capture data is processed by said processing means using forward dynamic simulations to predict moments of force, and wherein new control data is output to said motion platform system to produce a reactive physical environment;
    a memory section for recording said motion capture data and said motion platform data; and
    an interface means to said system with a runtime control input.

15. The system for dynamic registration, evaluation, and correction of functional human behavior, according to claim 14, further comprising a means for playing back said motion capture data and said motion platform data from said memory section.

16. The system for dynamic registration, evaluation, and correction of functional human behavior, according to claim 15, wherein said memory section contains a library of previously recorded data.

17. The system for dynamic registration, evaluation, and correction of functional human behavior, according to claim 15, wherein said playing back of said motion platform data from said memory section generates external forces on said user.

18. The system for dynamic registration, evaluation, and correction of functional human behavior, according to claim 14, further comprising a means for displaying a reactive virtual reality environment to said user.

* * * * *